United States Patent [19]
Waki

[11] Patent Number: 5,596,192
[45] Date of Patent: Jan. 21, 1997

[54] MASS SPECTROMETRIC APPARATUS FOR USE WITH A LIQUID CHROMATOGRAPH

[75] Inventor: Hiroaki Waki, Kyoto, Japan

[73] Assignee: Shimadzu Corporation, Japan

[21] Appl. No.: 631,948

[22] Filed: Apr. 15, 1996

[30] Foreign Application Priority Data

Apr. 28, 1995 [JP] Japan ..................... 7-129480

[51] Int. Cl.[6] ..................... H01J 49/04
[52] U.S. Cl. ............ 250/288; 250/281; 250/282
[58] Field of Search ............... 250/288, 288 A, 250/281, 282, 423 R, 396 R

[56] References Cited

U.S. PATENT DOCUMENTS

| | | | |
|---|---|---|---|
| 4,300,044 | 11/1981 | Iribarne et al. | 250/288 |
| 5,157,260 | 10/1992 | Mylchreest et al. | 250/288 |
| 5,164,592 | 11/1992 | Kitamori et al. | 250/288 |
| 5,432,343 | 7/1995 | Gulcicek et al. | 250/288 |

*Primary Examiner*—Jack I. Berman
*Assistant Examiner*—Kiet T. Nguyen
*Attorney, Agent, or Firm*—Majestic Parsons Siebert & Hsue

[57] ABSTRACT

A mass spectrometric apparatus receives a liquid sample from a liquid chromatograph, ionizes it under an atmospheric condition and guides these ions from the liquid sample along a specified trajectory through one or more intermediate vacuum chambers to a mass analyzer kept inside a high vacuum chamber. At least one of these intermediate vacuum chambers is kept in an intermediate vacuum condition in the so-called viscous flow region and contains at least one pair of mutually separated planar electrodes sandwiching the trajectory. Voltages of the same polarity as that of the ions which are passed through are adjustably applied to the electrodes so as to form a converged ion beam and also to control its trajectory. Two mutually perpendicular pairs of such electrodes may be disposed across the trajectory. Two sets each with two such pairs of electrodes may be disposed across the trajectory.

18 Claims, 2 Drawing Sheets

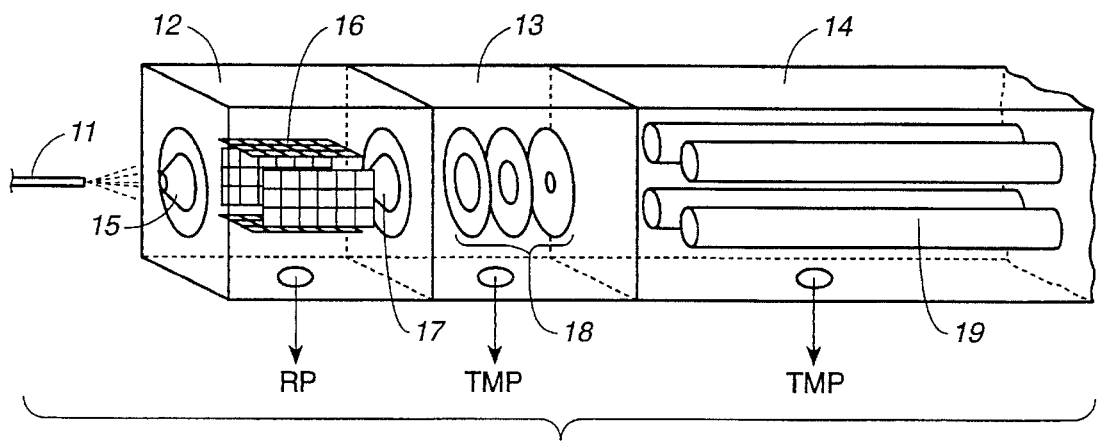
FIG._1
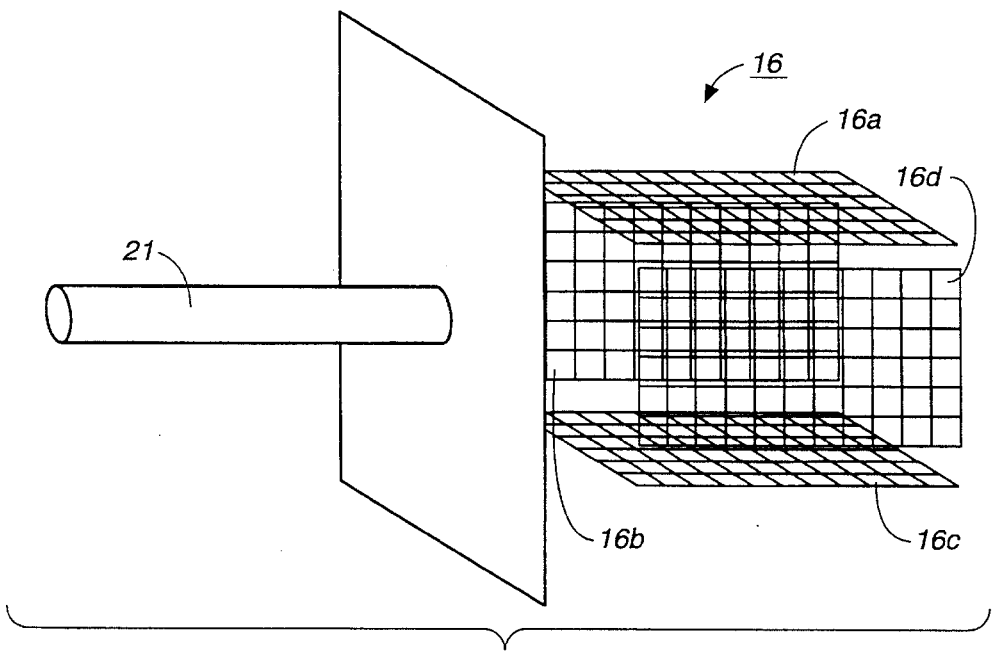
FIG._2

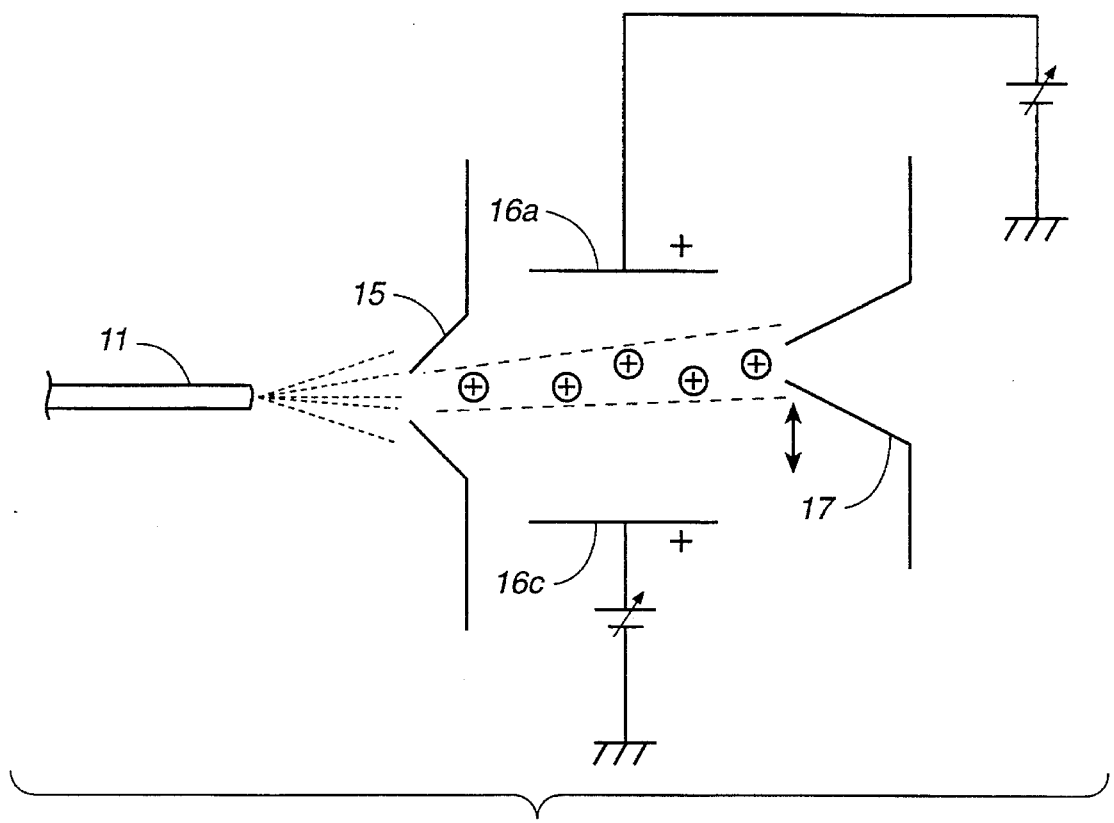
FIG._3
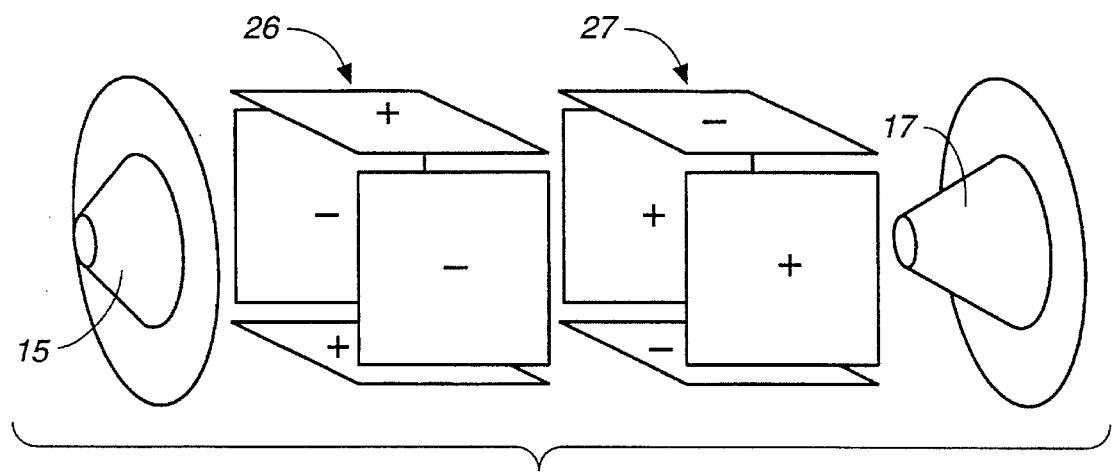
FIG._4

MASS SPECTROMETRIC APPARATUS FOR USE WITH A LIQUID CHROMATOGRAPH

BACKGROUND OF THE INVENTION

This invention relates to a mass spectrometric apparatus for use with a liquid chromatograph, receiving a liquid sample ionized under an atmospheric condition.

With a mass spectrometric apparatus for use with a liquid chromatograph using an atmospheric pressure ionization (API) method such as an electro-spray ionization (ESI) method or an atmospheric pressure chemical ionization (APCI) method, a component separated by the liquid chromatograph is ionized under an atmospheric condition and introduced to a mass spectrograph (such as of the quadrupole type or the magnetic field type) kept under a high vacuum condition inside a chamber (hereinafter referred to as the high vacuum chamber). Because the degree of vacuum required inside such a high vacuum chamber is about $10^{-5}$–$10^{-6}$ torr and a nozzle must be provided to the chamber such that the ions of the liquid sample can pass therethrough to reach the mass spectrograph, it is difficult to directly connect the high vacuum chamber to the atmospheric environment. It is therefore a common practice to provide an interface comprising one or more chambers (hereinafter referred to as intermediate vacuum chambers) disposed between the atmospheric environment and the high vacuum chamber and to carry out multi-stage differential gas evacuation in two or more stages.

The degree of vacuum in these intermediate vacuum chambers is necessarily between those of the atmospheric environment and the high vacuum chamber. Hydrodynamically, the degree of vacuum may be divided into so-called viscous flow and molecular flow regions. By the viscous flow is meant a layer flow wherein collisions between gas molecules dominate, while it is a molecular flow if collisions between the gas molecules and the inner wall of the container are dominant. In many examples of a mass spectrometric apparatus of this type used with a liquid chromatograph having two intermediate vacuum chambers between the atmospheric environment in which the liquid sample is ionized and the high vacuum chamber containing the mass spectrograph, the degree of vacuum in the first intermediate vacuum chamber (on the upstream side closer to the liquid chromatograph) is about 1 torr and that in the second intermediate vacuum chamber (on the downstream side closer to the high vacuum chamber) is about $10^{-3}$–$10^{-4}$ torr, the degree of vacuum inside the high vacuum chamber being about $10^{-5}$–$10^{-6}$ torr. The degree of vacuum of about 1 torr inside the first intermediate vacuum chamber is within the viscous flow region. That of about $10^{-3}$–$10^{-4}$ torr inside the second intermediate vacuum chamber is in the region of intermediate and molecular flows.

It now goes without saying that nozzles must be provided to all partition walls through which ions of the liquid sample must travel from the atmospheric environment outside the chambers to the high vacuum chamber. Because these nozzles are each provided to a partition wall between two chambers which must be maintained at different degrees of vacuum, their openings must be very small, say, less than 1 mm in diameter. This makes it difficult to produce such apparatus with a high level of productivity especially because these small nozzle openings must be accurately aligned.

A method has been proposed whereby nozzles on the downstream side are intentionally positioned off the line of alignment such that only low-mass ions can pass through the nozzles on the downstream end and that charged particles with large masses and neutral particles (clusters) are blocked. By this method, however, the number of ions capable of passing through the nozzles on the downstream end decreases significantly, adversely affecting the detection sensitivity of the apparatus.

SUMMARY OF THE INVENTION

It is therefore an object of this invention to overcome such problems of prior art technology by providing an improved mass spectrometric apparatus capable of allowing many ions to pass through both upstream and downstream nozzles even if they are positionally displaced from the line of alignment such that the drop in sensitivity can be limited to a minimum.

A mass spectrometric apparatus according to this invention for use with a liquid chromatograph, with which the above and other objects can be accomplished, may be characterized not only as ionizing a liquid sample from the liquid chromatograph under an atmospheric condition and having an interface with one or more intermediate vacuum chambers sandwiched between the liquid chromatograph and a high vacuum chamber containing a mass analyzer, but also as having at least one pair of planar electrodes disposed inside one of the intermediate vacuum chambers in the viscous flow region. The intermediate vacuum chamber has two nozzles, through one of which ions are adapted to enter and through the other of which they are to leave the chamber. The pair of electrodes are positioned so as to sandwich therebetween the trajectory of ions passing through the chamber, or the straight line connecting the two nozzles, and adjustable voltages of the same polarity as that of the ions which pass through the chamber are applied to these electrodes.

With a mass spectrometric apparatus thus structured, a liquid sample separated by the liquid chromatograph is ionized under an atmospheric condition and is passed through at least one intermediate vacuum chamber in the viscous flow region with a pair of electrodes before reaching the mass analyzer inside the high vacuum chamber. Because voltages of the same polarity as that of the ions are applied to these electrodes on mutually opposite sides of the ion trajectory, the ions are repelled by the voltages of the same polarity applied to both of the electrodes. With the voltages appropriately adjusted, the ions can be properly converged on the straight line connecting the two nozzles of the intermediate vacuum chamber. Thus, if the voltages are adjusted while measuring the number of ions which pass through the mass analyzer (or its detection output), the apparatus can be adjusted such that a maximum number of ions can pass the nozzle on the downstream side, independently of the relative positions of the nozzles, or whether or not the two nozzles of the chamber are correctly aligned. In other words, a maximum sensitivity can be obtained easily by adjusting the voltages.

Although it has not been unknown to place a pair of parallel electrodes inside an intermediate vacuum chamber of a mass spectrometric apparatus maintained at a higher degree of vacuum in the molecular flow region to control the direction of motion of ion flow from a liquid chromatograph, it has not been done to place such electrodes in an intermediate vacuum chamber in the viscous flow region. Ions move differently in the molecular flow and viscous flow regions. Since there are many collisions of ions with air molecules (that is, nitrogen and oxygen molecules) in the viscous flow region, as explained above, it has not been considered to control the trajectory of ions by an electrostatic field in the viscous flow region. Although U.S. Pat. No. 5,157,260 disclosed electrodes placed inside an intermediate vacuum chamber in the viscous flow region, it was only for the purpose of converging ions which otherwise tend to disperse. In the case of a cylindrical electrode, ions can be converged only to its center. Thus, if the position of the cylindrical electrode is fixed at the time of its production with its center displaced from the nozzle, its sensitivity will remain low and there is nothing that can be done to improve the situation. According to this invention, by contrast, use is made of a pair, or pairs, of mutually separate planar electrodes such that it is possible not only to converge the ions but also to change the trajectory of the ion beam by adjusting the voltages to be applied to the electrodes to thereby lead the ions to a desired position. In other words, even if there is an error in the positioning of the nozzle at the time of production, this error can be compensated for at the time of using the apparatus such that ions can correctly pass through both nozzles.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic drawing showing the structure of a mass spectrometric apparatus embodying this invention for use with a liquid chromatograph;

FIG. 2 is a schematic diagonal view of a portion of the apparatus of FIG. 1 when a heated metallic pipe is additionally used;

FIG. 3 is a schematic side view of the apparatus of FIG. 1 for showing the basic principle of the invention; and FIG. 4 is a schematic diagonal view of an electrode arrangement according to another embodiment of this invention for use in the apparatus of FIG. 1.

DETAILED DESCRIPTION OF THE INVENTION

FIGS. 1–3 show a mass spectrometric apparatus embodying this invention, comprising a high vacuum chamber 14 at a high degree of vacuum containing therein a mass analyzer 19 and two (first and second) intermediate vacuum chambers 12 and 13 in front (on the upstream side) of the high vacuum chamber 14. Although FIG. 1 shows a mass analyzer of the quadrupole type, this is not intended to limit the scope of the invention. This can also be replaced by a mass analyzer of the magnetic field type or the time-of-flight type. A sampling cone 15 is provided between the outside space and the first intermediate vacuum chamber 12, and a skimmer 17 is provided between the first intermediate vacuum chamber 12 and the second intermediate vacuum chamber 13, there being provided a nozzle with a small diameter at the tip of each in order to allow ions to pass therethrough. The interior pressure of the first intermediate vacuum chamber 12 is maintained at about 1 torr by means of a rotary pump (RP), while a turbo molecular pump (TMP) is used to maintain the internal pressure of the second intermediate vacuum chamber 13 at about $10^{-3}$–$10^{-4}$ torr. Similarly, the interior of the high vacuum chamber 14 is kept at about $10^{-5}$–$10^{-6}$ torr by means of a turbo molecular pump (TMP).

The example shown in FIG. 1 uses the so-called electrospray ionization (ESI) method such that a liquid sample separated by the liquid chromatograph is sprayed from a spray needle 11 as charged liquid droplets by a non-uniform electric field caused by a high voltage applied to the tip of the spray needle 11. The sprayed liquid droplets break up and become even smaller charged particles by the Coulomb repulsion within each droplet. Solvents are gradually removed as these small charged particles pass through the sampling cone 15, from the sampling cone 15 into the first intermediate vacuum chamber 12 and into the second intermediate vacuum chamber 13, becoming ionized during the process. As shown in FIG. 2, a heated metallic pipe (capillary) 21 may be disposed between the spray needle 11 and the sampling cone 15 such that the solvent can be removed more efficiently. The ionization of the sprayed liquid droplets may be effected alternatively by the so-called atmospheric pressure chemical ionization (APCI) method or any other ionization method.

Inside the first intermediate vacuum chamber 12, there are provided two pairs of planar mesh electrodes 16, one pair 16a and 16c being respectively above and below and the other pair 16d and 16b being respectively on the right-hand side and left-hand side of the paths of the ions. As shown in part in FIG. 3, direct current (DC) voltages of the same polarity as that of the ions that are passing through are applied to these electrodes 16. As a result, the charged particles and ions introduced from the sampling cone 15 into the first intermediate vacuum chamber 12 are repelled from these electrodes 16, converging at the center. By appropriately adjusting the DC voltages to be applied to the electrodes 16, the converged beam of the charged particles and ions can be directed to the nozzle of the skimmer 17. Such adjustments of voltages can be effected to correctly guide the ion beam to the nozzle of the skimmer 17 by varying the applied voltages while measuring the outputs from detectors (not shown) on the downstream side of the mass analyzer 19.

This invention can effectively improve productivity because any error in the positioning of the nozzles of the sampling cone 15 and the skimmer 17 at the time of assembly can be compensated for at the time of use. This invention also allows the user to intentionally dispose the nozzles eccentrically with respect to each other so as to selectively inhibit the passage of certain charged particles, for example, by adjusting the applied voltages appropriately such that only those ions with the charge-to-mass ratio greater than a certain value can pass through.

The ions which have passed the first intermediate vacuum chamber 12 are made convergent by ion lenses 18 disposed inside the second intermediate vacuum chamber 13, have their acceptance controlled as dictated by the mass analyzer 19 and are injected into the high vacuum chamber 14.

The example described above is intended to be illustrative and not intended to limit the scope of the invention. The electrodes 16 may be formed with metallic plates with ventilating openings in order to effectively remove the solvent from the liquid particles. The electrodes 16 need not necessarily be completely flat. They may be arcuate, or cylindrical, for example, so as to surround the axial path of the ions, although it is preferable to separate the electrode into several parts around the axial path such that the trajectory of the ions can be varied.

FIG. 4 shows another example embodying the invention, characterized as having two pairs of planar electrodes at two places, the one at an upstream position being indicated by numeral 26 and the other at a downstream position by numeral 27. Onto the mutually perpendicular pairs of the upstream electrodes 26, voltages of mutually opposite polarities are applied such that the cross-sectional shape of the ion beam passing therethrough will be flattened (in a direction dependent on the polarity of the ions). Voltages of opposite polarities are applied to the pairs of the downstream electrodes 27 such that the cross-sectionally flattened ion beam will be further converged and their cross-sectional shape will approach that of a point.

In summary, many modifications and variations are possible within the scope of this invention, and such modifications and variations that may be apparent to a person skilled in the art are intended to be within the scope of this invention.

What is claimed is:

1. A mass spectrometric apparatus for receiving a liquid sample from a liquid chromatograph, ionizing said liquid sample under an atmospheric condition and guiding ions from said liquid sample along a specified trajectory to a mass analyzer inside a high vacuum chamber in a high vacuum condition, said mass spectrometric apparatus comprising:

one or more intermediate vacuum chambers between said liquid chromatograph and said high vacuum chamber, at least one of said intermediate vacuum chambers being an electrode-containing chamber with degree of vacuum in viscous flow region, said electrode-containing chamber having two nozzles on mutually opposite partition walls thereof corresponding to said trajectory and containing therein a pair of mutually separated planar electrodes, said trajectory being sandwiched between said pair of electrodes; and voltage means for individually and adjustably applying to said electrodes voltages of same polarity as that of said ions which enter said electrode-containing chamber through one of said nozzles.

2. The mass spectrometric apparatus of claim 1 wherein said electrode-containing chamber contains therein a first pair and a second pair of mutually separated planar electrodes, the electrodes of both said first and second pairs sandwiching said trajectory therebetween in mutually perpendicular directions, said voltage means being adapted to individually and adjustably apply voltages of same polarity as that of said ions to the electrodes of both said first and second pairs.

3. The mass spectrometric apparatus of claim 1 wherein said electrode-containing chamber contains therein a first electrode set and a second electrode set sequentially along said trajectory, each of said electrode sets having a first pair and a second pair of mutually separated planar electrodes, the first pairs of electrodes of said first and second electrode sets sandwiching said trajectory in a first direction, the second pairs of electrodes of said first and second electrode sets sandwiching said trajectory in a second direction, said first and second directions being perpendicular to said trajectory and also to each other, said voltage means being adapted to individually and adjustably apply voltages of same polarity as that of said ions to the electrodes of said first pair of said first electrode set and said second pair of said second electrode set and voltages of opposite polarity to said second pair of said first electrode set and said first pair of said second electrode set.

4. The mass spectrometric apparatus of claim 1 further comprising a heated metallic pipe around said trajectory between said liquid chromatograph and said intermediate vacuum chambers for removing solvent components from said liquid sample.

5. The mass spectrometric apparatus of claim 1 wherein each of said electrodes have ventilating openings.

6. The mass spectrometric apparatus of claim 1 wherein said high vacuum chamber is in vacuum condition of about $10^{-5}$–$10^{-6}$ torr, and said intermediate vacuum chambers are in vacuum condition of about 0.1–$10^{-4}$ torr.

7. A method of mass spectroscopy comprising the steps of:

ionizing in an atmospheric condition a liquid sample from a liquid chromatograph;

leading ions from said liquid sample through one or more intermediate vacuum chambers along a specified trajectory to a mass analyzer inside a high vacuum chamber, at least one of said intermediate vacuum chambers being an electrode-containing chamber with degree of vacuum in viscous flow range, said electrode-containing chamber containing therein a pair of mutually separated planar electrodes, said trajectory being sandwiched between said pair of electrodes; and applying to said electrodes voltages of same polarity as that of said ions.

8. The method of claim 7 further comprising the step of adjusting said voltages to obtain a desired degree of detection sensitivity for said mass analyzer.

9. The method of claim 7 wherein said electrode-containing chamber contains therein a first pair and a second pair of mutually separated planar electrodes, the electrodes of both said first and second pairs sandwiching said trajectory therebetween in mutually perpendicular directions, voltages of same polarity as that of said ions being applied to electrodes of both said first and second pairs.

10. The method of claim 9 further comprising the step of adjusting said voltages to obtain a desired degree of detection sensitivity for said mass analyzer.

11. The method of claim 9 further comprising the step of maintaining said high vacuum chamber at about $10^{-5}$–$10^{-6}$ torr and said intermediate vacuum chambers at about 0.1–$10^{-4}$ torr.

12. The method of claim 9 further comprising the step of causing said liquid sample to pass through a heated metallic pipe to cause evaporation of solvent components.

13. The method of claim 7 wherein said electrode-containing chamber contains therein a first electrode set and a second electrode set sequentially along said trajectory, each of said electrode sets having a first pair and a second pair of mutually separated planar electrodes, the first pairs of electrodes of said first and second electrode sets sandwiching said trajectory in a first direction, the second pairs of electrodes of said first and second electrode sets sandwiching said trajectory in a second direction, said first and second directions being perpendicular to said trajectory and also to each other, said step of applying voltages comprising individually and adjustably applying voltages of same polarity as that of said ions to the electrodes of said first pair of said first electrode set and said second pair of said second electrode set and individually and adjustably applying voltages of opposite polarity to said second pair of said first electrode set and said first pair of said second electrode set.

14. The method of claim 13 further comprising the step of adjusting said voltages to obtain a desired degree of detection sensitivity for said mass analyzer.

15. The method of claim 13 further comprising the step of maintaining said high vacuum chamber at about $10^{-5}$–$10^{-6}$ torr and said intermediate vacuum chambers at about 0.1–$10^{-4}$ torr.

16. The method of claim 13 further comprising the step of causing said liquid sample to pass through a heated metallic pipe to cause evaporation of solvent components.

17. The method of claim 7 further comprising the step of maintaining said high vacuum chamber at about $10^{-5}$–$10^{-6}$ torr and said intermediate vacuum chambers at about 0.1–$10^{-4}$ torr.

18. The method of claim 7 further comprising the step of causing said liquid sample to pass through a heated metallic pipe to cause evaporation of solvent components.

* * * * *